(12) United States Patent
Doi et al.

(10) Patent No.: US 7,276,361 B2
(45) Date of Patent: Oct. 2, 2007

(54) METHOD FOR PRODUCING BIODEGRADABLE POLYESTER

(75) Inventors: Yoshiharu Doi, Saitama (JP); Seiichi Taguchi, Saitama (JP); Tomoyasu Kichise, Saitama (JP)

(73) Assignee: Riken, Saitama (JP)

( * ) Notice: Subject to any disclaimer, the term of this patent is extended or adjusted under 35 U.S.C. 154(b) by 437 days.

(21) Appl. No.: 10/498,049

(22) PCT Filed: Dec. 9, 2002

(86) PCT No.: PCT/JP02/12840

§ 371 (c)(1),
(2), (4) Date: Jun. 9, 2004

(87) PCT Pub. No.: WO03/050277

PCT Pub. Date: Jun. 19, 2003

(65) Prior Publication Data

US 2005/0009949 A1 Jan. 13, 2005

(30) Foreign Application Priority Data

Dec. 9, 2002 (JP) .............................. 2001-376237

(51) Int. Cl.
*C12N 15/01* (2006.01)
*C12P 7/62* (2006.01)
(52) U.S. Cl. ................... 435/135; 435/183; 435/252.3; 435/254.2; 435/829; 536/23.2
(58) Field of Classification Search ................ 435/183, 435/252.3, 254.2, 829; 536/23.2
See application file for complete search history.

(56) References Cited

U.S. PATENT DOCUMENTS 5,245,023 A * 9/1993 Peoples et al. ............ 536/23.2
5,534,432 A * 7/1996 Peoples et al. ............. 800/298
5,663,063 A * 9/1997 Peoples et al. ............. 435/135
5,750,848 A * 5/1998 Kruger et al. ............... 800/281
6,103,956 A * 8/2000 Srienc et al. ................ 800/298
6,143,952 A * 11/2000 Srienc et al. ................ 800/298
6,228,623 B1 * 5/2001 Asrar et al. .................. 435/135

FOREIGN PATENT DOCUMENTS

EP 824148 A2 2/1998
JP 2002-099890 A 7/2002

OTHER PUBLICATIONS

Taguchi, S. et al., "Analysis of Mutational of a Polyhydroxybutyrate (PHB) Polymerase on Bacterial PHB Accumulation Using an In Vivo Assay System", FEMS Mictobiol. Lett. Apr. 2001, vol. 198, No. 1, pp. 65-71.
Fukui, T. et al., "Cloning and Analysis of the Poly (3-Hydroxybutyrate-Co-3-Hydroxyhexanoate) Biosynthesis Genes of *Aeromonas caviae*", J. Bacteriol. Aug. 1997, vol. 179, No. 15, pp. 4821-4830.
Kichise, T. et al., Enhanced Accumulation and Changed Monomer Composition in Polyhydroxyalkanoate (PHA) Copolyester by In Vitro Evolution of *Aeromonas caviae* PHA Synthase, Appl. Environ. Microbiol. May 2002, vol. 68, No. 5, pp. 2411-2419.
Jia et al., Biochemistry, vol. 39, No. 12, 2000, pp 3927-3936.

* cited by examiner

*Primary Examiner*—Herbert J. Lilling
(74) *Attorney, Agent, or Firm*—Birch, Stewart, Kolasch & Birch, LLP

(57) ABSTRACT

There is provided a method for producing a biodegradable polyester capable of controlling various physical properties of the biodegradable polyester. A poly(3-hydroxyalkanoate) biosynthetic enzyme is altered by an evolutionary-engineering technique, and the poly(3-hydroxyalkanoate) biosynthetic enzyme is expressed in a host to synthesize various copolymers in the host.

11 Claims, 8 Drawing Sheets

METHOD FOR PRODUCING BIODEGRADABLE POLYESTER

This application is a 371 of PCT/JP02/12840 filed Dec. 9, 2002 which claims benefit to Japan 2001-376237 filed Dec. 10, 2001.

TECHNICAL FIELD

The present invention relates to a method for producing a biodegradable polyester capable of controlling various physical properties thereof, a method for producing a biodegradable polyester having desired physical properties, a biodegradable polyester obtained by the method and a poly(3-hydroxyalkanoate) biosynthetic mutant enzyme capable of producing the biodegradable polyester having desired physical properties.

BACKGROUND ART

Creation of environment-conscious biodegradable plastics has attracted attention as part of constructing sustainable society. Poly(3-hydroxyalkanoates) (PHAs) produced by microorganisms such as *Ralstonia eutropha*, which have both thermoplasticity and biodegradability, have been studied for the application as biodegradable plastics and have already been put to practical use in part.

It is important to construct a less expensive production system and breed microorganisms which can freely produce biodegradable plastics having desired physical properties in order to put biodegradable plastics to practical use more widely. In order to achieve the above, various attempts have been carried out such as a search for a new type of biodegradable polyester synthase, an increase in the production volume of the enzyme by genetic-engineering techniques and metabolism-engineering alteration of the biosynthesis path way in cells.

For example, when a biodegradable plastic is a copolymer, various physical properties of the biodegradable plastics can be controlled by the compositional ratio of monomers. However, a technique to effectively alter the compositional ratio of monomers in a copolymer has not yet been established and so biodegradable plastics having desired physical properties have not yet been obtained.

Recently, an evolutionary-engineering technique has been used to alter the properties of enzymes. The evolutionary-engineering technique means the engineering use of Darwin's principle of evolution. Specifically, it is a method for acquiring enzymes with desired properties by rapidly carrying out a step, in vitro, comprising artificially inducing mutations in a gene encoding a target enzyme, selecting a gene encoding the enzyme which is altered to a desired activity among numbers of mutant genes and amplifying the selected gene. This method has been applied to the alteration of enzymes for detergents and the like, and several successful examples have already been reported. However, applications to alteration of enzymes in the production of biodegradable plastics are not known.

Thus, it is an object of the present invention to provide a method for producing a biodegradable polyester capable of controlling various physical properties thereof, a method for producing a biodegradable polyester having desired physical properties, a biodegradable polyester obtained by the method and a poly(3-hydroxyalkanoate) biosynthetic mutant enzyme capable of producing the biodegradable polyester having desired physical properties.

DISCLOSURE OF THE INVENTION

As a result of diligent investigation for the purpose of solving the above problems, the present inventors have come to achieve the present invention by succeeding in altering an enzyme involved in the biosynthesis of poly(3-hydroxyalkanoates) to the enzyme with desired properties by an evolutionary-engineering technique.

The present invention includes the followings:

(1) A method for producing a biodegradable polyester, comprising; modifying a poly(3-hydroxyalkanoate) biosynthetic enzyme by an evolutionary-engineering technique; and expressing the modified poly(3-hydroxyalkanoate) biosynthetic enzyme in a host to synthesize a copolymer in the host.

(2) The method for producing a biodegradable polyester according to (1), wherein the host biosynthesizes a copolymer of 3-hydroxybutyrate and 3-hydroxyalkanoate having a carbon number of 3-14.

(3) A method for producing a biodegradable polyester, comprising, expressing a poly(3-hydroxyalkanoate) biosynthetic mutant enzyme in a host to synthesize a copolymer in the host, wherein the poly(3-hydroxyalkanoate) biosynthetic mutant enzyme being produced by substituting other amino acids for the 149th asparagine and/or the 171st aspartic acid in a poly(3-hydroxyalkanoate) biosynthetic enzyme comprising the amino acid sequence of SEQ ID No: 1.

(4) The method for producing a biodegradable polyester according to (3), wherein the poly(3-hydroxyalkanoate) biosynthetic mutant enzyme is prepared by substituting serine for the 149th asparagine.

(5) The method for producing a biodegradable polyester according to (3), wherein the poly(3-hydroxyalkanoate) biosynthetic mutant enzyme is prepared by substituting glycine for the 171 st asparagine.

(6) A biodegradable polyester produced by the method for producing a biodegradable polyester described in any one of (1) to (5).

(7) A poly(3-hydroxyalkanoate) biosynthetic mutant enzyme, comprising substitution of other amino acids for the 149th asparagine and/or the 171st aspartic acid in a poly(3-hydroxyalkanoate) biosynthetic enzyme comprising the amino acid sequence of SEQ ID No: 1.

(8) The poly(3-hydroxyalkanoate) biosynthetic mutant enzyme according to (7), wherein the 149th amino acid is serine.

(9) The poly(3-hydroxyalkanoate) biosynthetic mutant enzyme according to (7), wherein the 171 st amino acid is glycine.

This specification includes part or all of the contents as disclosed in the specification and/or drawings of Japanese Patent Application No. 2001-376237, which is a priority document of the present application.

BEST MODE FOR CARRYING OUT THE INVENTION

Hereinafter, the present invention will be described in detail.

A method for producing a biodegradable polyester according to the present invention comprises altering a poly(3-hydroxyalkanoate) biosynthetic enzyme by an evolutionary-engineering technique and then expressing the poly(3-hydroxyalkanoate) biosynthetic enzyme altered by the evolutionary-engineering technique in a predetermined host to synthesize a copolymer in the host.

As herein described "poly(3-hydroxyalkanoate) biosynthetic enzyme" refers to a key enzyme essential for the synthesis of polyester, which is the enzyme in catalyzing the polymerization of (R)-3-hydroxyacyl-CoA monomer. Poly (3-hydroxyalkanoates) are polymers in which 3-hydroxyalkanoates are linked to each other by ester linkages, with 3-hydroxyalkanoates as constituting units, and mean ester polymers which are biosynthesized by organisms and decomposed by microorganisms in soil and in water.

Figure 1:
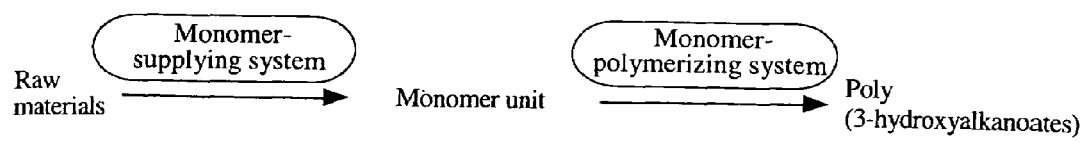
FIG. 1 shows a scheme for the biosynthesis of poly(3-hydroxyalkanoates)
Figure 2:
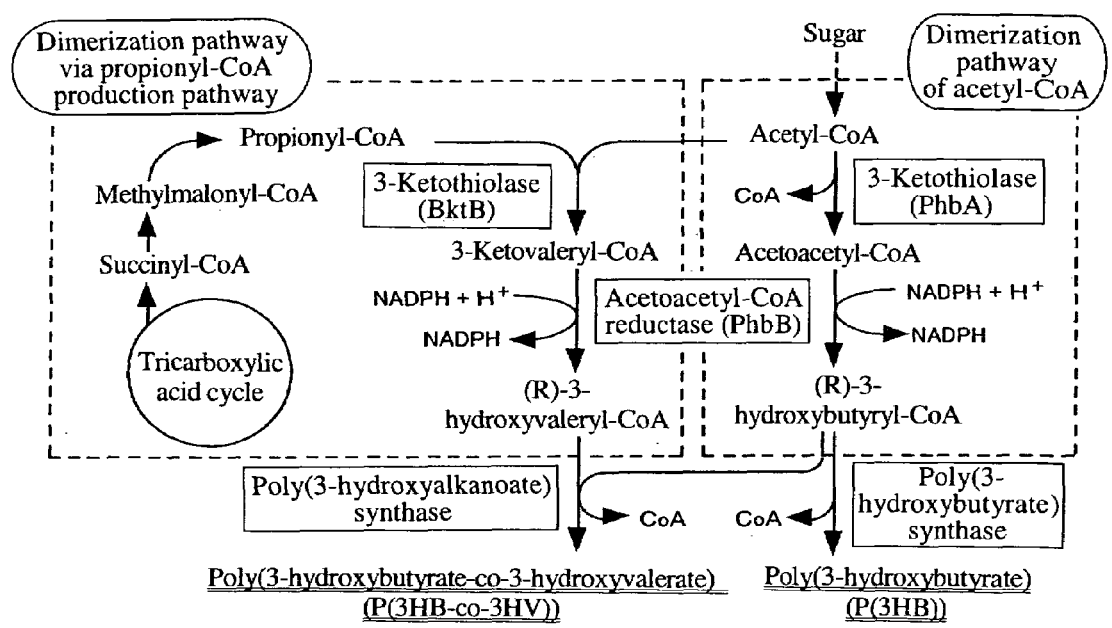
FIG. 2 shows the production of polyesters from the acetyl-CoA dimerization system in bacteria and enzymes involved therein.
Figure 3:
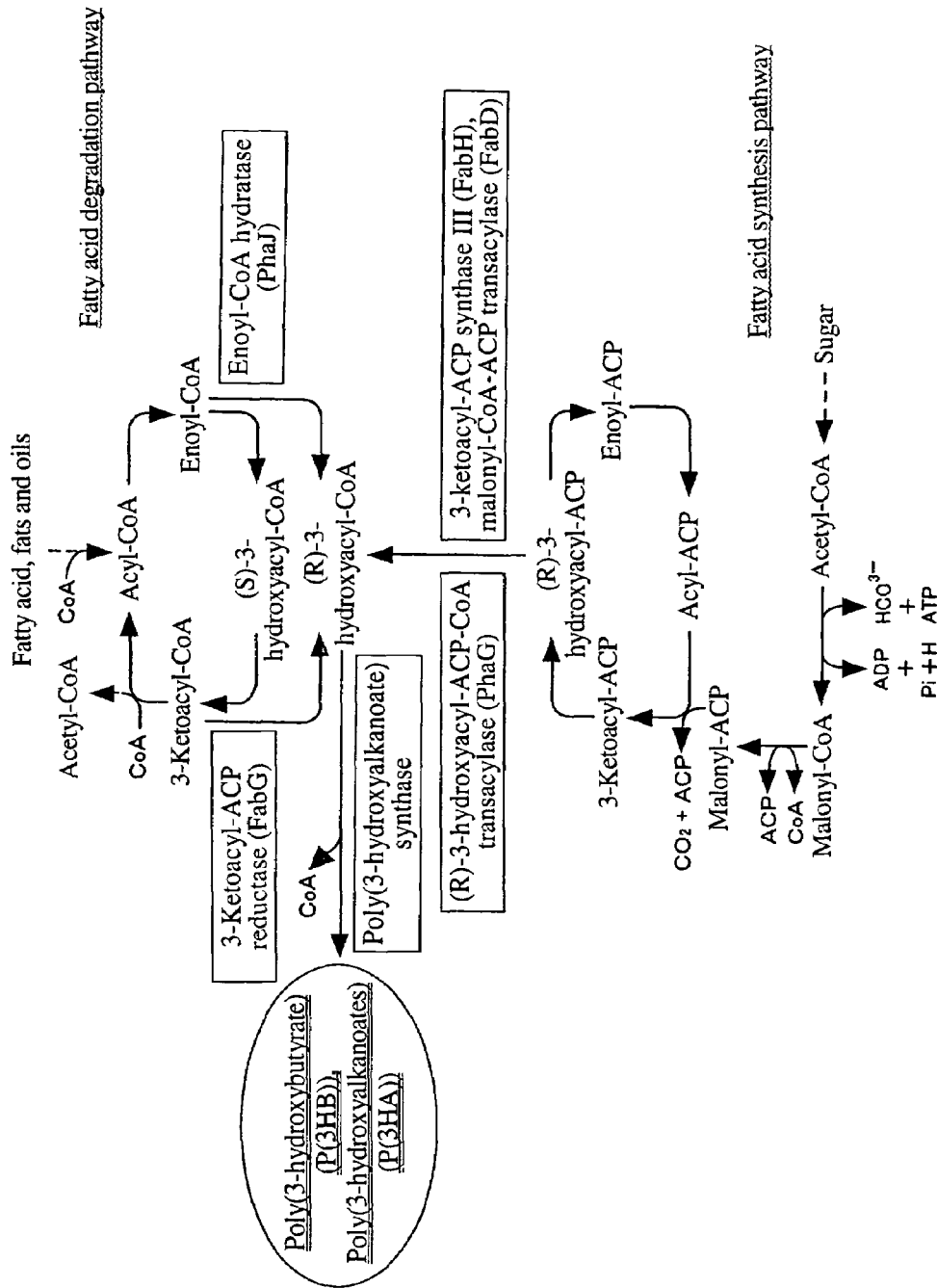
FIG. 3 shows the production of polyesters from the fatty acid metabolism system in bacteria and enzymes involved therein.

The biosynthetic pathway of poly(3-hydroxyalkanoates) in bacteria generally consists of two systems, a system for supplying monomer units for constituting poly(3-hydroxyalkanoates) (monomer-supplying system) and a system for polymerizing the monomer units (monomer polymerizing system), as shown in FIG. 1. For example, the biosynthesis of poly(3-hydroxyalkanoates) in bacteria is carried out by polymerizing biosynthesized monomer units using a poly (3-hydroxybutyrate) synthase or a poly(3-hydroxyalkanoate) synthase. As shown in FIGS. 2 and 3, the monomer units ((R)-3-hydroxyvaleryl-CoA and (R)-3-hydroxybutyril-CoA in FIG. 2; (R)-hydroxyacyl-CoA in FIG. 3) are biosynthesized through the acetyl-CoA dimerization system comprising 3-ketothiolase (PhbA, BktB), acetoacetyl-CoA reductase (PhbB) and the like; the fatty acid degradation pathway comprising enoyl-CoA hydratase (PhaJ), 3-ketoacyl-ACP reductase (FabG) and the like; the fatty acid biosynthetic pathway comprising (R)-3-hydroxyacyl-ACP-CoA transacylase (PhaG), 3-ketoacyl-ACP synthase III (FabH), malonyl-CoA-ACP transacylase (FabD) and the like. Here, poly(3-hydroxybutyrate) refers to a homopolymer of 3-hydroxybutyrate; and poly(3-hydroxyalkanoates) refer to wide range of homopolymers of 3-hydroxyalkanoates comprising various monomer units such as hydroxybutyrate having a carbon number of 4, hydroxyvalerate having a carbon number of 5, hydroxyhexanoate having a carbon number of 6, hydroxyheptanoate having a carbon number of 7, hydroxyoctanoate having a carbon number of 8, hydroxynonanoate having a carbon number of 9, hydroxydecanoate having a carbon number of 10 and hydroxydodecanoate having a carbon number of 12.

A poly(3-hydroxyalkanoate) biosynthetic enzyme is a polymerase in which 3-hydroxyalkanoates having a carbon number of 3 to 14 serve as substrates. A poly(3-hydroxybutyrate) biosynthetic enzyme is a polymerase in which short chain 3-hydroxyalkanoates having a carbon number of 3 to 5 serve as substrates. Therefore, the poly(3-hydroxyalkanoate) biosynthetic enzyme can be called the enzyme having wide substrate specificity compared with the poly(3-hydroxybutyrate) biosynthetic enzyme.

Meanwhile, as described herein "evolutionary-engineering technique" refers to a technique for altering a target protein molecule by artificially inducing mutations in vitro in a gene encoding the target protein and then selecting the protein whose properties are altered to desired properties. The alteration of poly(3-hydroxyalkanoate) biosynthetic enzyme by the evolutionary-engineering technique can be carried out specifically as described below.

Figure 4:
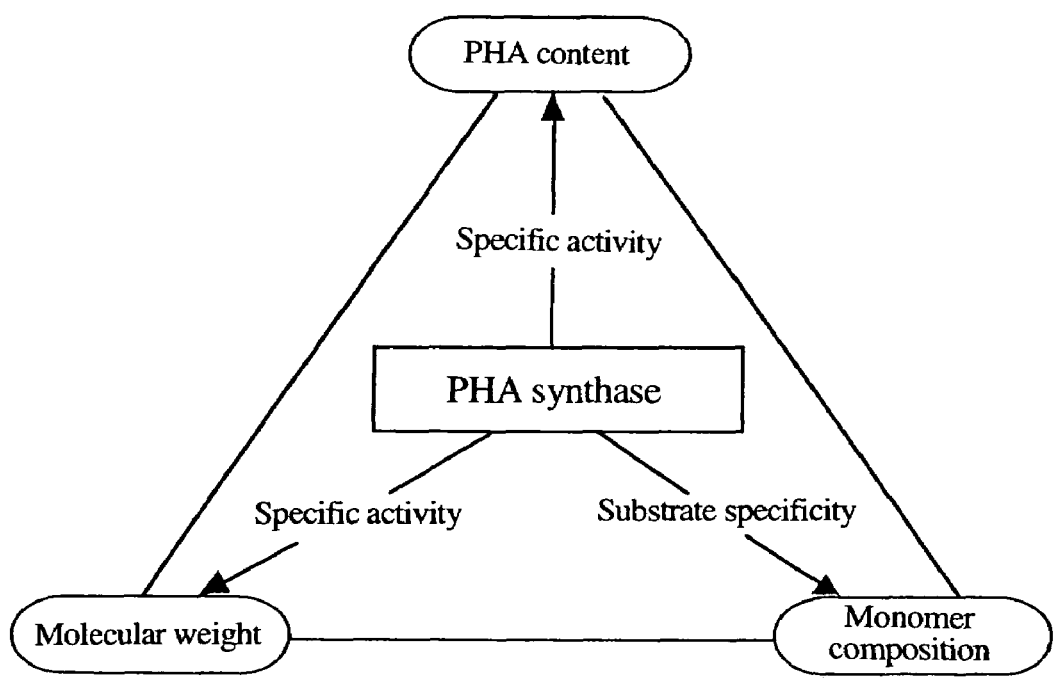
FIG. 4 shows the influence of enzymological properties of poly(3-hydroxyalkanoate) biosynthetic enzymes on the physical properties and productivity of poly(3-hydroxyalkanoates) to be produced.

1. Modification of poly(3-hydroxyalkanoate) Biosynthetic Enzyme by Evolutionary Engineering (1) Poly(3-hydroxyalkanoate) Biosynthetic Enzyme The specific activity of a poly(3-hydroxyalkanoate) biosynthetic enzyme (described as "PHA synthase" in FIG. 4) influences the intracellular content of poly(3-hydroxyalkanoates) to be produced (described as "PHA content" in FIG. 4) and the molecular weight of poly(3-hydroxyalkanoates), and the substrate specificity of a poly(3-hydroxyalkanoate) biosynthetic enzyme influences the monomer composition, as shown in FIG. 4. Therefore, the alteration of the specific activity and substrate specificity of the enzyme can alter the intracellular content, molecular weight and monomer content of poly(3-hydroxyalkanoates) to be produced.

For example, the poly(3-hydroxyalkanoate) synthase $PhaC_{AC}$ derived from *Aeromonas caviae* (the amino acid sequence is shown in SEQ ID No: 1.) is subjected to modification by evolutionary engineering alteration in the present method. The present method is not limited to the poly(3-hydroxyalkanoate) synthase $PhaC_{AC}$, but can be applied to poly(3-hydroxyalkanoate) synthase PhaC1 derived from *Pseudomonas* sp. 61-3 strain, poly(3-hydroxyalkanoate) synthase PhaC2 derived from the same bacterium and the like. The DNA encoding each of the above enzymes can be easily acquired by well known techniques such as PCR using genome DNA or cDNA derived from each microorganism as a template.

The $PhaC_{AC}$ can synthesize not only a poly(3-hydroxybutyrate) homopolymer, but also a random copolymer of 3-hydroxybutyrate and 3-hydroxyhexanoate from carbon sources such as alkanoates or fats and oils. The poly(3-hydroxybutyrate) homopolymer has rigid and brittle properties, but the random copolymer of 3-hydroxybutyrate and 3-hydroxyhexanoate has received attention as a useful biodegradable polyester as it has more flexible properties. Thus, the molecular breeding of $PhaC_{AC}$ is expected to be very effective for the study of controlling the copolymer composition and improving the productivity.

(2) Random Mutagenesis

A mutant gene encoding the poly(3-hydroxyalkanoate) biosynthetic mutant enzyme having desired properties is acquired by randomly introducing mutations into the gene encoding a poly(3-hydroxyalkanoate) biosynthetic enzyme. The random introduction of mutations into the gene encoding the above enzyme can be carried out as described below by using a mutagen, radiation, a PCR method and the like. Specifically, it can be carried out by exposing microorganisms containing the gene of a target enzyme to chemicals such as base analogs such as 5-bromouracil, 5-chlorouracil and bromodeoxyuridine; nitrous acid inducing oxidative deamination of nucleic acid bases; hydroxyamines reacting with cytosine/guanine; and alkylation reagents such as mustard gas and N-methyl-N'-nitro-N-nitrosoguanidine. In addition, the random mutagenesis by radiation can be introduced by exposing microorganisms containing the gene of a target enzyme to radiation such as ultraviolet rays and X-rays.

Moreover, the random mutagenesis by a PCR method can be introduced by the so-called error-prone PCR method in which, in the amplification reaction of the gene encoding the poly(3-hydroxyalkanoate) biosynthetic enzyme using the DNA fragments containing a part or the whole of the above gene as a template, PCR is carried out in a condition where the fidelity of the replication reaction of DNA polymerase is reduced to accumulate replication errors in amplified DNA sequences. Here, the fidelity of the replication reaction can be controlled by setting the pH in the DNA polymerase reaction to the alkali side, setting the concentration of magnesium ions in the reaction system to higher values than usual, changing the bivalent metal ion to be added from magnesium ions to manganese ions, or changing the concentration of four types of deoxynucleoside 5'-triphosphates (4×NTP) as substrates. For example, the pH in the error-prone PCR is preferably from 8.3 to 8.8, most preferably from 8.5 to 8.8. Further, the concentration of magnesium ions in the error-prone PCR is from 15 to 50 mM, preferably 50 mM.

For example, when mutation of the poly(3-hydroxyalkanoate) synthase PhaC$_{AC}$ derived from *Aeromonas caviae* by the error-prone PCR method is intended, the PCR is carried out under conditions for reducing the fidelity by using a plasmid containing a part or all of the gene encoding the gene as template and a primer for the amplification of the above enzyme gene. The resultant PCR fragments are then linked to a suitable expression vector to be introduced into a host cell (for example, *Escherichia coli*). Then, the alteration of the above enzyme is verified by verifying the properties of a mutation-treated enzyme contained in the resultant host cell, into which the vector is introduced.

(3) Verification of the Enzymological Properties of Mutant Enzymes

The change in the enzymological properties of the poly (3-hydroxyalkanoate) biosynthetic enzyme obtained in the above described (2) can be carried out by comparing each mutant enzyme to the wild type enzyme before alteration for enzymological parameters such as specific activity, substrate specificity, optimum temperature, optimum pH, temperature stability and pH stability, after separation/purification as required.

The specific activity of the 3-hydroxyalkanoate biosynthetic mutant enzyme can be investigated in the manner as described below. Specifically, CoA-SH liberated when (R)-3-hydroxybutyryl-CoA is incorporated into the enzyme is determined by measuring the increase of absorbance at 412 nm associated with the oxidation to TNB$^-$ of DTNB (5,5'-dithiobis(2-nitrobenzoic acid) which reacts with CoA-SH in an equal molar ratio, and the specific activity of the poly (3-hydroxyalkanoate) biosynthetic mutant enzyme can be calculated by the equations shown below:

$$\text{Activity (U/ml)} = \frac{\Delta A_{412}/\text{minute}}{\varepsilon_{412}} \times 10^3 \times \frac{V_T}{V_E}$$

$$\text{Specific activity (U/mg)} = \frac{\text{Activity (U/ml)}}{\text{Protein concentration (mg/ml)}}$$

In the above equations, $V_T$ denotes the reaction solution volume (ml); $V_E$ denotes the enzyme solution volume (ml); $\varepsilon_{412}$ is $15.6\times10^3$ (M$^{-1}\cdot$cm$^{-1}$); and $\Delta A_{412}$/minute denotes the difference of absorbance per one minute. For other enzymes, which can be also the object of the modification by evolutionary engineering according to the present invention, their specific activity can be measured according to the literature known in the art.

Moreover, the substrate specificity of the poly(3-hydroxyalkanoate) biosynthetic mutant enzyme can be investigated by using various types of substrates and measuring the specific activities thereto in the above measuring method.

On the other hand, when the gene encoding the poly(3-hydroxyalkanoate) biosynthetic enzyme has been mutated by the error-prone PCR method, the host cell transformed by the expression vector, to which mutation-treated PCR fragments obtained by the error-prone PCR method are linked, are cultured under conditions allowing the production of poly(3-hydroxyalkanoates) to investigate the state of production and accumulation of poly(3-hydroxyalkanoates) in the cell. For example, the state of production and accumulation of poly(3-hydroxyalkanoates) can be determined by investigating the degree of pink coloration of colonies grown on an agar plate by allowing the plate to contain Nile Red which specifically dyes poly(3-hydroxybutyrate). Here, the higher degree of coloration can be assessed as the higher intracellular content of poly(3-hydroxybutyrate), and can be assessed as the higher activity of the poly(3-hydroxyalkanoate) biosynthetic enzyme. In addition, it can also be observed with high sensitivity by the intensity of fluorescence emitted by photoirradiation at 312 nm [Spickermann et al. Arch Microbiol., 171: 73-80 (1999)].

Furthermore, the precise determination of the content of poly(3-hydroxybutyrate) in each clone can be carried out in the following manner. Specifically, when the content of poly(3-hydroxybutyrate) is about 1% or more in terms of the weight of dry cells, the determination can be carried out by a method in which poly(3-hydroxybutyrate) is extracted from cells with an organic solvent (for example, chloroform) and then subjected to methanolysis in a methanol-concentrated sulfuric acid solution, and methylated 3-hydroxybutyrate is analyzed by gas chromatography (GC). When the content of poly(3-hydroxybutyrate) is less than about 1% in terms of the weight of dry cells, the determination can be carried out by a method or the like in which poly(3-hydroxybutyrate) is converted to crotonic acid (elimination reaction) by concentrated sulfuric acid under high temperature, and the crotonic acid is supplied to high-performance liquid chromatography (HPLC) to be separated from other components for spectroscopic detection of the absorption at 210 nm [Karr et al.: Appl. Environ. Microbiol., 46: 1339-1344 (1983); Seebach et al.: Eur. J. Biochem., 224: 317-328 (1994)].

In this connection, the fact that the evolutionary-engineering technique can provide the poly(3-hydroxyalkanoate) biosynthetic mutant enzyme, in which enzymological properties are changed in various manners, can be clarified by drawing the fitness landscape, for example, with the enzyme activity (alternatively, stability to various environments) as the ordinate and the clone number as the abscissa.

(4) Identification of the Amino Acid Site Contributing to the Alteration of Enzymological Properties For the clone in which the change of enzymological properties is observed in the above (3), the base sequence of the gene encoding the poly(3-hydroxyalkanoate) biosynthetic mutant enzyme is determined, and the estimated amino acid sequence is compared to the wild type amino acid sequence. This comparison can identify the functional mapping, that is, which amino acid on the enzyme protein contributes to the alteration of enzymological properties. The base sequence can be determined by the techniques known in the art (for example, dideoxy chain termination method) using an automatic sequencer (for example, DNA sequencer model 373A available from PERKIN-ELMER Corporation).

Here, when a plurality of amino-acid substitutions are identified on the amino acid sequence of the poly(3-hydroxyalkanoate) biosynthetic mutant enzyme in which the alteration of enzymological properties is found, it is possible to investigate to what extent respective amino acid substitutions contribute to the alteration of enzymological properties by preparing a single-point mutant enzyme (a mutant in which a different amino acid is substituted for only one amino acid on the enzyme protein) by genetic-engineering techniques. Specifically, the region containing the site which is intended to be mutated on the DNA encoding the enzyme is removed by a restriction enzyme, and the DNA fragment containing the codon which is singly replaced by a desired amino acid is inserted instead, thereby allowing preparation of the DNA encoding the mutant type enzyme containing only one amino acid substitution. The degree of contribution by the amino acid which influences enzymological properties can be investigated by ligating the DNA to a suitable expression vector to be introduced into a host, expressing the single-point mutant enzyme in the host and comparing the enzymological properties thereof to those of the wild type enzyme.

(5) Site-Specific Saturation Mutagenesis

Introduction of the site-specific saturation mutagenesis into the amino-acid site contributing the enzymological properties found in the above (4) allows optimization to the enzyme with desired properties. The introduction of the site-specific saturation mutagenesis into a target enzyme gene can be carried out using a recombinant DNA technology, a PCR method or the like, as described below. Specifically, the introduction of mutations by a recombinant DNA technology can be carried out by cassette mutagenesis in which, for example, when there exist suitable restriction enzyme recognition sequences at both sides of the target site to which the introduction of mutations is desired, in the poly(3-hydroxyalkanoate) biosynthetic enzyme gene, the restriction enzyme recognition sequences are cut by the restriction enzyme; the region containing the site to which the introduction of mutations is desired is removed; and then the DNA fragment in which mutations are introduced only into the target site by chemical synthesis or the like is inserted. Further, the introduction of the site-specific saturation mutagenesis by PCR can be carried out by amplifying one side of the poly(3-hydroxyalkanoate) biosynthetic enzyme gene using a mutant primer in which a target mutation is introduced into the target site in the above gene where the introduction of mutations is desired and an amplification primer having no mutation which contains the sequence of one terminal site of the above gene, amplifying the other side using a mutant primer having a complementary sequence to the above mutant primer and an amplification primer having no mutation which contains the sequence of the other terminal site of the above gene, annealing the obtained two amplified fragments, and then further carrying out PCR using the above two types of amplification primers [SHORT PROTOCOLS IN MOLECULAR BIOLOGY, 3$^{rd}$ ed, 1995, F. A. Susubel et al., WILEY]. The resultant site-specific saturation mutagenesis constructs are investigated for enzymological properties in the above (3) and investigated for the activity of the enzyme which is altered to desired properties, and clones containing the enzyme having desired properties are selected.

2. Preparation of Recombinant Vector and Transformant

The recombinant vector which can express the poly(3-hydroxyalkanoate) biosynthetic mutant enzyme in a predetermined host can be obtained by linking the gene encoding the poly(3-hydroxyalkanoate) biosynthetic mutant enzyme obtained in the above "1. Modification of poly(3-hydroxyalkanoate) biosynthetic enzyme by evolutionary engineering" to a suitable vector. In addition, a transformant which can express the poly(3-hydroxyalkanoate) biosynthetic mutant enzyme can be obtained by introducing the obtained recombinant vector into a predetermined host.

A vector for inserting a gene is not particularly limited as long as it can be autonomously replicated in a predetermined host, and specifically plasmid DNA and phage DNA can be used as the vector. For example, when *Escherichia coli* is used as a host, plasmid DNAs such as pBR322, pUC18 and pBluescript II, phase DNAs such as EMBL3, M13 and λgt11 and the like; when yeast is used as a host, YEp13, YCp50 and the like; when a vegetable cell is used as a host, pBI121, pBI101 and the like; when an animal cell is used as a host, pcDNAI, pcDNAI/Amp (Invitrogen Corporation) and the like can be used as the vector.

A host for introducing the recombinant vector is not limited as long as it can polymerize 3-hydroxyalkanoates by ester linkages using 3-hydroxyalkanoates as constitutional units to synthesize poly(3-hydroxyalkanoates), and can includes, for example, *Escherichia coli* strains of the LS series such as LS5218(fadR$^-$), LS1298(fabB$^-$), LS1300(fre) and LS6596 (fadA30). These *Escherichia coli* strains of the LS series are mutant strains in which fadR, the minus control factor in enzyme genes associated with the fatty acid β-oxidation pathway, is destroyed, and are characterized in that they can metabolize fatty acids more efficiently than other *Escherichia coli*. In addition, even typical *Escherichia coli* can be used as the host by adding acrylic acid (optimum concentration 0.24 mg/ml) to inhibit the fatty acid β-oxidation pathway.

A method for introducing recombinant vectors into bacteria may include, for example, a method of using calcium ions [Current Protocols in Molecular Biology, vol. 1, page 1.8.1, 1994], the electroporation method [Current Protocols in Molecular Biology, vol. 1, page 1.8.4, 1994] and the like. A method for introducing recombinant vectors into yeast may include, for example, the electroporation method [Methods Enzymol., 194, 182-187 (1990)], the spheroplast method [Proc. Natl. Acad. Sci. USA, 84, 1929-1933 (1978)], the lithium acetate method [J. Bacteriol., 153, 163-168 (1983)] and the like. A method for introducing recombinant vectors into vegetable cells may include the *Agrobacterium* infection method, the particle gun method, the polyethylene glycol method and the like. A method for introducing recombinant vectors into animal cells may include, for example, the electroporation method, the calcium phosphate method and the like.

3. Production of poly(3-hydroxyalkanoate) Biosynthetic Mutant Enzyme

The poly(3-hydroxyalkanoate) biosynthetic mutant enzyme of the present invention may be produced by culturing the transformant of the present invention in a medium, forming and accumulating the enzyme in the culture (cultured cell or culture supernatant) and collecting the enzyme from the culture.

The method for culturing the transformant in a medium may be carried out according to conventional methods used for culturing hosts. The medium for culturing the transformant obtained by using bacteria such as *Escherichia coli* as a host may include a complete medium or a synthetic medium, for example, the LB medium, the M9 medium and the like. In addition, the poly(3-hydroxyalkanoate) biosynthetic mutant enzyme may be accumulated in bacteria cells and recovered by aerobically culturing the same for 12 to 14 hours at a culture temperature of 37° C.

Carbon sources are required for the growth of microorganisms, and they may include, for example, carbohydrates such as glucose, fructose, sucrose and maltose. Nitrogen sources may include, for example, ammonium salts such as ammonia, ammonium chloride, ammonium sulfate and ammonium phosphate, peptone, meat extract, yeast extract, corn steep liquor and the like. In addition, inorganic substances may include, for example, primary potassium phosphate, secondary potassium phosphate, magnesium phosphate, magnesium sulfate, sodium chloride and the like. Antibiotics such as kanamycin, ampicillin and tetracycline may be added in a medium, as required for a selection pressure for holding plasmid.

The purification of the poly(3-hydroxyalkanoate) biosynthetic mutant enzyme may be carried out by recovering the obtained culture by centrifugation (cells are broken by a sonicator), and using affinity chromatography, cation- or anion-exchange chromatography, gel filtration or the like, singly or in combination. The identification that the obtained purified substance is the target enzyme may be carried out by conventional methods, for example, SDS polyacrylamide gel electrophoresis, western blotting and the like.

4. Production of Biodegradable Polyester

Biodegradable polyester can be produced by culturing the transformant obtained in the above 2 in a suitable medium. If the obtained poly(3-hydroxyalkanoate) biosynthetic mutant enzyme is used, a copolymer having desired properties can be produced in the transformant.

Here, the copolymer may include, for example, copolymers of 3-hydroxybutyrate (3HB) and 3-hydroxyalkanoates (3HA), for example, the copolymer of 3HB and 3-hydroxyhexanoate (3HHx). Hereinafter, the copolymer of 3HB and 3HA may be described as "P(3HB-co-3HA)", and the copolymer of 3HB and 3HHx as "P(3HB-co-3HHx)".

Specifically, P(3HB-co-3HA) can be produced by culturing the transformant obtained in the above 2 in a suitable medium. For example, in the above 2, when *Escherichia coli* LS5218 is used as a host, P(3HB-co-3HHx) can be produced in the cell.

In the transformant obtained in the above 2, the accumulation level of P(3HB-co-3HA) is enhanced, and it is possible to produce P(3HB-co-3HA) with a different composition ratio from the case where the wild type poly(3-hydroxyalkanoate) biosynthetic enzyme is used. Particularly, it is possible to synthesize the poly(3-hydroxyalkanoates) with the enhanced accumulation level of P(3HB-co-3HA) and high composition ratio of 3HA by expressing the poly(3-hydroxyalkanoate) biosynthetic enzyme which is evaluated as having high activity using the intracellular content of poly(3-hydroxybutyrate) as the index, in the above 1. The poly(3-hydroxyalkanoate) becomes a flexible material due to a higher composition ratio of 3HA, and shows practically excellent properties.

The intracellular content of polyesters accumulated in cells and the composition of polyesters can be measured/analyzed by extracting polyesters with an organic solvent such as chloroform and subjecting the extract to gas chromatography, NMR and the like, according to the method by Kato et al. [Kato, M. et al., Appl. Microbiol. Biotechnol. 45, 363 (1996); Kato, M. et al., Bull. Chem. Soc. Jpn. 69, 515 (1996)].

EXAMPLES

Hereinafter, the present invention will be specifically described by illustrating examples, but the scope of the present invention is not limited to these examples.

Example 1

Alteration of poly(3-hydroxyalkanoate) Biosynthetic Enzyme by Error-Prone PCR

Figure 5:
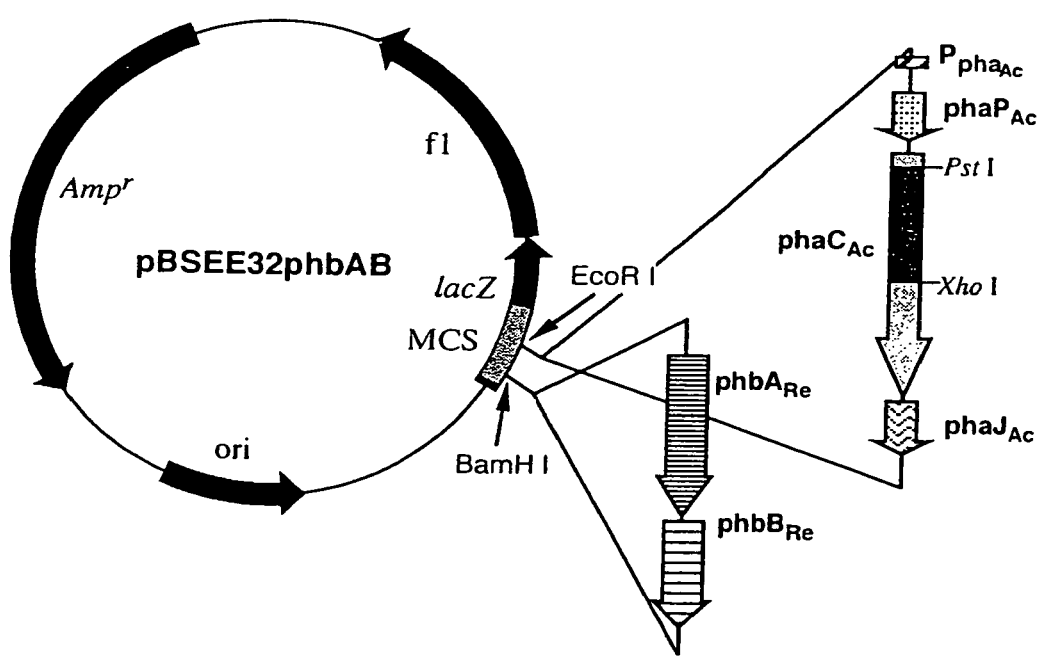
FIG. 5 shows the structure of plasmid pBSEE32phbAB.

Random mutagenesis was introduced into the PstI-XhoI region in the gene (PhaC$_{AC}$) encoding the poly(3-hydroxyalkanoate) biosynthetic enzyme derived from *Aeromonas caviae* FA440 by the error-prone PCR method. In the error-prone PCR method, an attempt was made to introduce mutations to the whole PstI-XhoI region in PhaC$_{AC}$ without limiting the place of the mutations by carrying out the PCR under a condition where the fidelity for the incorporation of substrates by polymerase is reduced, using the forward primer 5'-gctgctgcagaccaatc-3' (SEQ ID No: 2) containing the restriction enzyme PstI recognition sequence and the reverse primer 5'-gcctcattttgcgcctcg-3' (SEQ ID No: 3) containing the restriction enzyme XhoI recognition sequence, and using the plasmid vector pBSEE32phbAB (Refer to FIG. 5) containing PhaC$_{AC}$ as a template. For the PCR, the reaction solution was prepared so that it has the composition shown in Table 1.

TABLE 1

| | |
|---|---|
| 100 mM TriS—HCl (pH 8.8) | 10 µl |
| 500 mM KCl | 10 µl |
| 1 mg/ml BSA | 10 µl |
| 50 mM MgCl$_2$ | 10 µl |
| 10 mM dATP | 2 µl |
| 10 mM dGTP | 2 µl |
| 10 mM dCTP | 2 µl |
| 10 mM dTTP | 2 µl |
| pBSEE32phbAB (ca. 5 ng) | 10 µl |
| forward and reverse primer (10 µl) | 5 µl each |
| DMSO | 10 µl |
| TaKaRa Taq DNA polymerase | 0.5 µl |
| ddH$_2$O | 21.5 µl |
| Total | 100 µl |

The PCR was carried out by 25 cycles, wherein each of the temperature cycle of the PCR consists of thermal denaturation for one minute at 94° C., annealing for one minute at 50° C. and elongation reaction for two minutes at 72° C. Gene Amp PCR system 9700 (available from Perkin-Elmer Applied Biosystems) was used for the PCR.

Then, the amplified DNA fragments obtained by the PCR were purified and isolated before they were treated with PstI and XhoI. Then, the molecular group (a pool of mutant clones) of mutant type PhaC$_{AC}$ was obtained by inserting by substitution the DNA fragments treated with the restriction enzyme into the restriction site of the original plasmid vector pBSEE32phbAB. The molecular group of mutant type PhaC$_{AC}$'s contains various PhaC$_{AC}$'s in which mutations are randomly introduced into the PstI-XhoI region.

The plasmid vector pBSEE32phbAB containing the mutant type PhaC$_{AC}$ obtained by the above operation was transformed into the competent cell of the *Escherichia coli* JM109 strain. The transformed cells were plated on LB agar media containing Nile Red which can specifically dye poly(3-hydroxybutyrate), glucose and ampicillin (Nile Red 0.5 µg/ml, glucose 2%, ampicillin 50 µg/ml, trypton 1%, yeast extract 0.5%, NaCl 1% and pH 7.0) and cultured for 14 hours at 37° C. to select transformed cells. The accumulation level of poly(3-hydroxybutyrate) produced in each transformed cell was estimated by the degree of pink coloration.

As a result, it was found that the capability of PHB synthesis in about 15% of 8,337 clones formed on the LB agar media was inactivated by the above introduction of mutations. Further, active clones were classified to three classes consisting of the S-class having the activity that is equal to the wild-type level, the M-class having the activity that is a little lower than the wild-type level and the L-class having the activity that is clearly lower than the wild-type level. According to this classification, 145 clones belonged to the S-class, 4,350 clones to the M-class and 2,755 clones to the L-class.

Next, the PHB content in 145 clones belonging to the S-class, 129 clones belonging to the M-class, 23 clones belonging to the L-class and 3 inactive clones were analyzed using HPLC (total 300 clones). The analysis thereof by HPLC was carried out after intracellular PHB was converted to crotonic acid by concentrated sulfuric acid treatment.

Specifically, cells were collected with 1.5 ml micro-tube, frozen and then subjected to freeze drying. After measuring the weight of dry cells, PHB in cells was converted to crotonic acid by concentrated sulfuric acid. The conversion of PHB to crotonic acid was carried out by adding 1 ml of concentrated sulfuric acid to the dry cells in the micro-tube, heating the mixture for 40 minutes at 120° C., and then rapidly cooling the same in ice. In this procedure, PHB in cells undergoes dehydration reaction by concentrated sulfuric acid under high temperature and converted to crotonic acid.

Next, the cooled sample was diluted with a four-fold amount of the 0.014 N sulfuric acid solution and further cooled, and the resultant sample was served as the HPLC sample. The sample was filtered with a filter comprising a hydrophilic PVDF membrane with a pore size of 0.45 µm, and then 10 µl of the sample was injected to the HPLC apparatus. Shimadzu LC-10 Avp system was used as the HPLC apparatus. Bio-rad Aminex HPX-87H (300×7.8 mm), which is a styrene-divinylbenzene copolymer cation exchange resin column with a degree of crosslinking of 8%, was used as a column. In addition, Bio-rad Cation-H Refill Cartridge (30×4.6 mm) was used as a guard column. A 0.014 N sulfuric acid solution was used as a mobile phase, and the measurement was carried out at a flow rate of 0.7 ml/min. The column temperature was set at 60° C., and the absorption at 210 nm derived from the carbonyl group of crotonic acid formed by dehydration reaction was spectroscopically detected. The retention time of crotonic acid was 20.4 minutes. The PHB accumulation rate was calculated on the basis of the relational expression of the amount of crotonic acid and the area (calibration curve).

Figure 6:
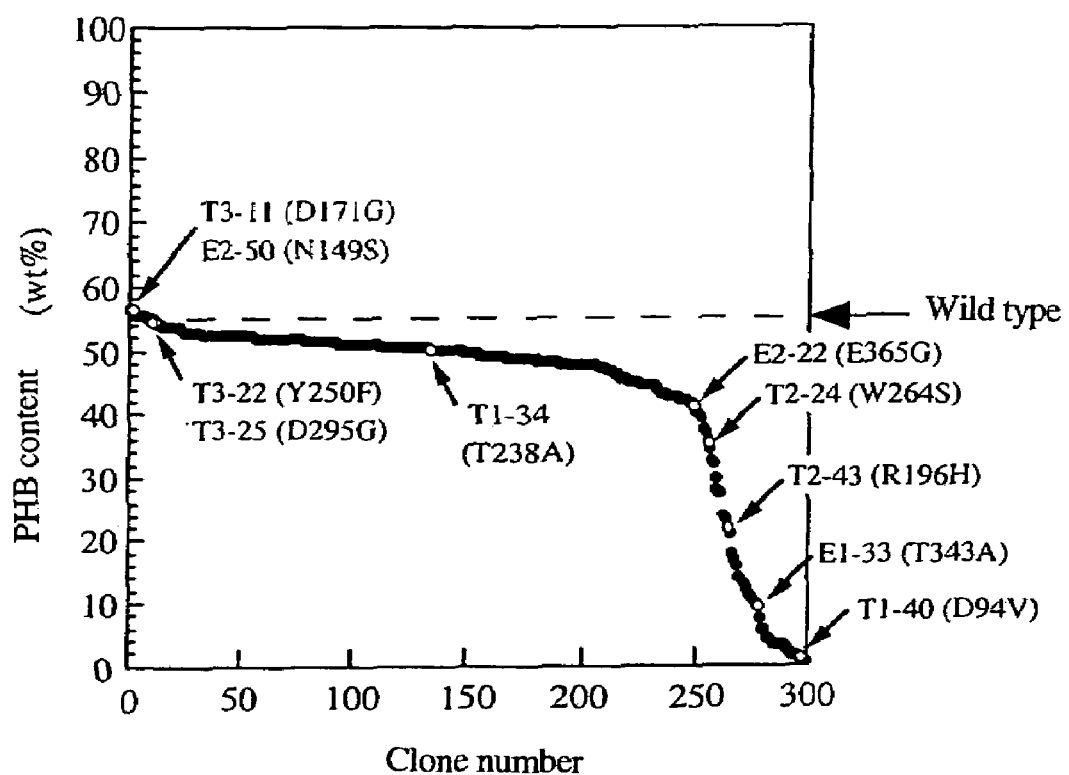
FIG. 6 shows the results of the PHB accumulation level measured using HPLC for 300 clones as a fitness landscape.

The results of the PHB accumulation level measured using the HPLC apparatus for 300 clones is shown in FIG. 6. FIG. 6 is a figure showing a so-called fitness landscape, with the PHB accumulation level as the ordinate and the clone number as the abscissa. In FIG. 6, the broken line shows the PHB level in the wild type *Escherichia coli* JM109.

The poly(3-hydroxyalkanoate) biosynthetic enzyme activity was determined for 10 clones indicated by the arrows in FIG. 6.

For determining the poly(3-hydroxyalkanoate) biosynthetic enzyme activity, each *E. coli* JM109 harboring each plasmid was first cultured for 14 hours in the LB medium containing 50 µg/ml of ampicillin which is a condition where polyesters are not accumulated. Then, the resultant cells were collected, washed with 20 mM sodium phosphate buffer (pH 7.2) containing 1 mM EDTA, redispersed in 200 µl of the above buffer and subjected to ultrasonic wave crushing (5 sec×5). The crushed liquid was subjected to centrifugation for 10 minutes at 18,000×g and 4° C. to obtain a soluble fraction. Then, the polymerization activity to (R)-3-hydroxybutyril-CoA ((R)-3HB-CoA) in the obtained soluble fraction was spectroscopically determined, and this polymerization activity was defined as the poly(3-hydroxyalkanoate) biosynthetic enzyme activity.

The polymerization activity was determined by the method as described below in which CoA-SH liberated in the polymerization reaction was quantified using DTNB, Ellman's reagent, with reference to the method described in Gerngross T. U. et al., Biochemistry 33: 9311-9320. In this method, the liberation reaction of CoA-SH was not determined continuously with time, but the polymerization reaction was stopped by adding trichloroacetic acid (TAC) to the reaction system per unit time to denature the protein, and the amount of the liberated CoA-SH until the reaction is stopped was quantified. The use of this method can eliminate the time when DTNB having thiol aggressiveness coexists with the enzyme having cysteine as the activation center in the reaction solution, and is advantageous in allowing quantitative determination with a small amount of liberated CoA-SH.

A mixture comprising sterile water, 1 M potassium phosphate buffer (pH 7.0) and 4.08 mM (R)-3BH-CoA was preheated for 10 minutes at 25° C., and a soluble fraction solution was added to the mixture to start reaction. After continuing the reaction for a predetermined period of time, 20 µl was sampled before stopping the reaction by 50 µl of 5% TCA. The reaction solution was centrifuged for 10 minutes at 4° C. and 15,000 rpm to obtain a soluble fraction. 62.5 µl of the resultant soluble fraction was added with 337.5 µl of 500 mM potassium phosphate buffer (pH 7.5) and 5 µl of 10 mM DTNB (dissolved in 500 mM potassium phosphate buffer (pH 7.5)). The mixture was left standing for two minutes at room temperature and TNB anions formed was determined at 412 nm. The amount of the enzyme which forms 1 µmol of TNB anion per one minute was defined as IU of the poly(3-hydroxyalkanoate) biosynthetic enzyme activity.

Figure 7:
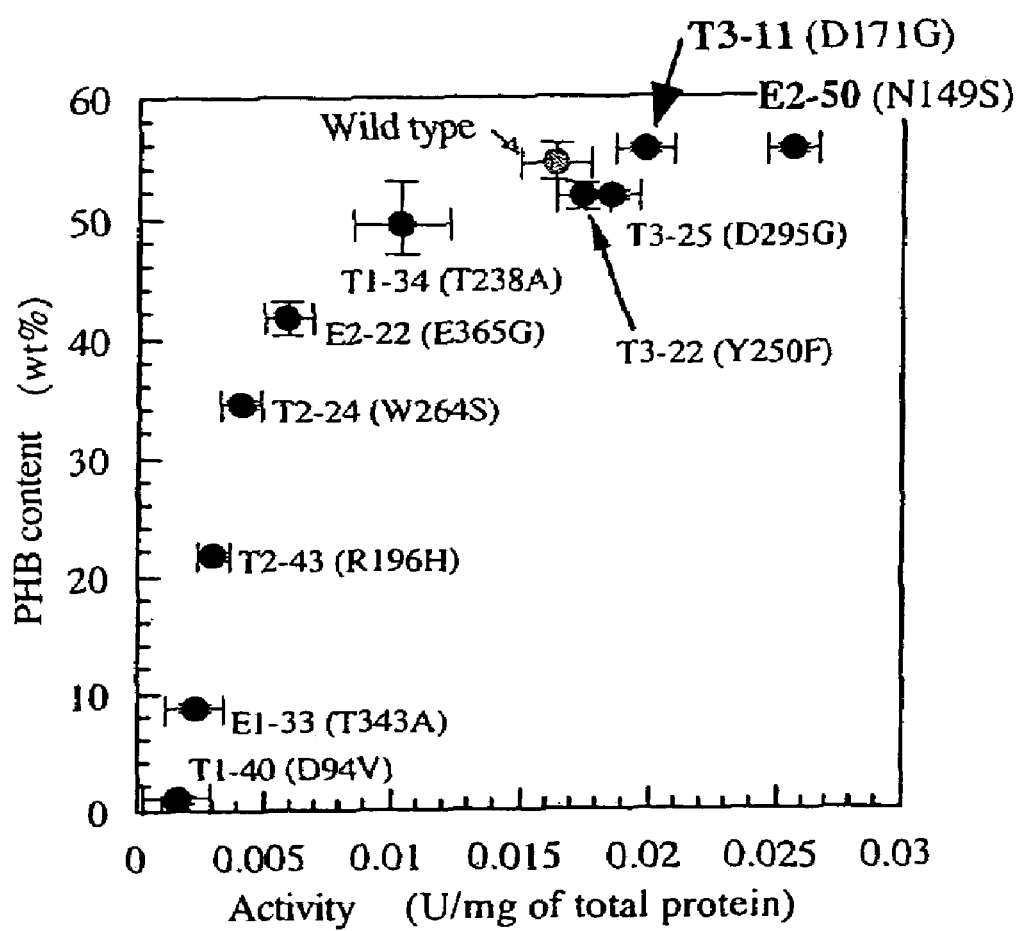
FIG. 7 shows the results of the poly(3-hydroxyalkanoate) biosynthetic enzyme activity measured for 10 clones.

The results of the poly(3-hydroxyalkanoate) biosynthetic enzyme activity measured for 10 clones are shown in FIG. 7. As shown in FIG. 7, in the relation of the poly(3-hydroxyalkanoate) biosynthetic enzyme activity and the PHB accumulation level, the PHB accumulation level increases maintaining linear relation with the activity up to around 45% by weight thereof. However, when the PHB accumulation level exceeds about 55% by weight, the PHB accumulation level does not keep up with the increase of poly(3-hydroxyalkanoate) biosynthetic enzyme activity. This suggests that the supply of monomers constructing PHB in cells is not sufficient.

In addition, as shown in FIG. 7, it was found that clones named as E2-50 and T3-11 had a higher poly(3-hydroxyalkanoate) biosynthetic enzyme activity than the wild type, and had about the same PHB accumulation level as the wild type. Further, it was found that clones named as T3-22 and T3-25 had a higher poly(3-hydroxyalkanoate) biosynthetic enzyme activity than the wild type, but had a lower PHB accumulation level as the wild type.

Figure 8:
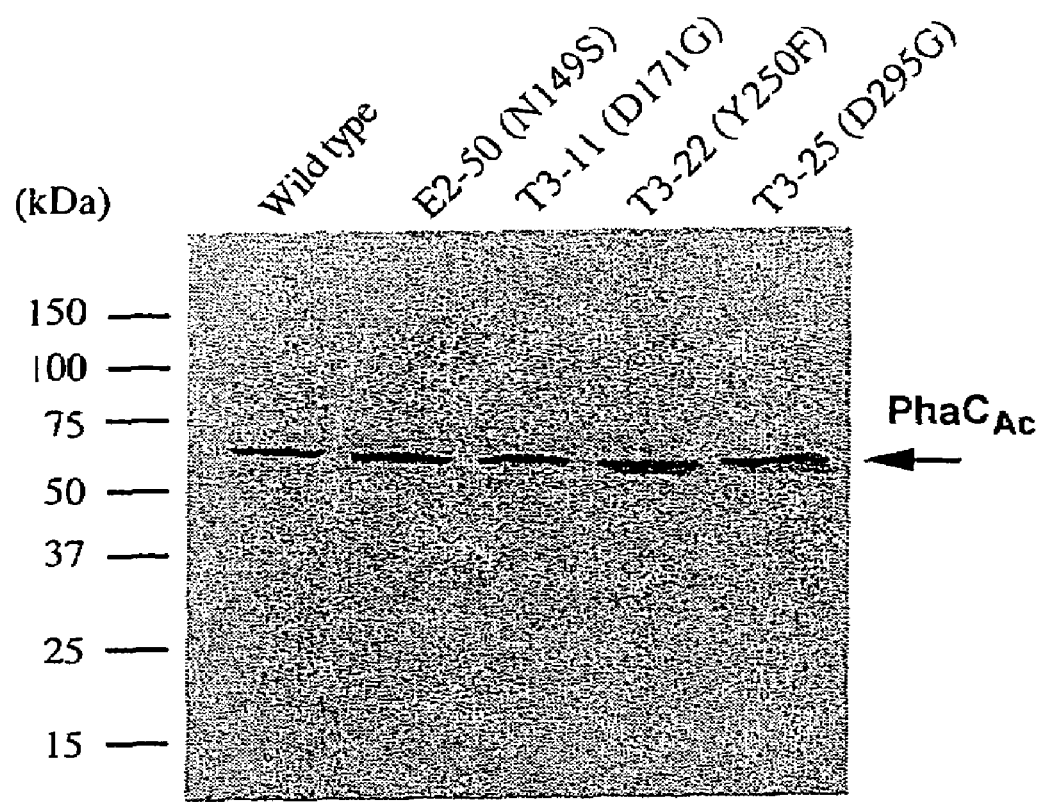
FIG. 8 shows the results of the western blotting which was carried out by using antisera which specifically recognize oligopeptides at the C-terminal of $PhaC_{AC}$ and are combined with the same.

The expression level of the poly(3-hydroxyalkanoate) biosynthetic enzyme in the above E2-50, T3-11, T3-22 and T3-25 was determined by the western blotting method. In the western blotting method, cell extracts containing 10 μg of soluble proteins were supplied to SDS-PAGE and antisera, which specifically recognize oligopeptides at the C-terminal of PhaC$_{AC}$ and are combined with the same, were used. FIG. 8 shows the results of the western blotting method. As can be understood from FIG. 8, the above E2-50, T3-11, T3-22 and T3-25 have expressed the poly(3-hydroxyalkanoate) biosynthetic enzyme at an equal level to the wild type.

As shown in the above results, the introduction of mutations into the PstI-XhoI region in PhaC$_{AC}$ derived from *Aeromonas caviae* FA440 using the error-prone PCR method allowed obtaining clones E2-50 and T3-11 having the poly(3-hydroxyalkanoate) biosynthetic enzyme which has a higher activity than the wild type and can accumulate more PHB than the wild type when sufficient amount of monomer is supplied.

Example 2

*Escherichia coli* LS5218 was transformed with mutant type PhaC$_{AC}$ contained in each of ES-50 and T3-11 obtained in Example 1. The accumulation level of P(3HB-co-3HHx) copolymer and the monomer composition composing P(3HB-co-3HHx) in the transformed *Escherichia coli* LS5218 were studied. It is known that *Escherichia coli* LS5218 can synthesize P(3HB-co-3HHx) copolymer from dodecanoate. *Escherichia coli* LS5218 was obtained from *E. coli* Genetic Stock Center (deposit number CGSC 6966).

Plasmid vector pBSEE32phbAB containing the mutant type PhaC$_{AC}$ was first purified for each of E2-50 and T3-11 obtained in Example 1 according to the method by Miller. The purified plasmid vector pBSEE32phbAB was then used to transform *Escherichia coli* LS5218. The transformed *Escherichia coli* LS5218 was cultured in a M9 medium containing 10 mM of dodecanoate and 50 μg/ml of ampicillin for 72 hours at 37° C. The composition of the M9 medium is shown in Table 2.

TABLE 2

| | |
|---|---|
| Na$_2$HPO$_4$•12H$_2$O | 17.4 g |
| KH$_2$PO$_4$ | 3 g |
| NaCl | 0.5 g |
| NH$_4$Cl | 1 g |
| 1 M MgSO$_4$ | 2 ml |
| 1 M CaCl$_2$ | 0.1 ml |
| 1% (w/v) thiamine | 1.0 ml |
| 20% (w/v) Brij35 | 20 ml |
| sodium dodecanoate (final 10 mM) | 2.22 g |

After culturing, the content of P(3HB-co-3HHx) copolymer in cells and the fraction of 3HHx monomer composing the P(3HB-co-3HHx) copolymer were determined. For determining the content of P(3HB-co-3HHx) copolymer and the fraction of 3HHx monomer, about 30 mg of dry cells were first subjected to methanolysis by treating the same with a solution consisting of 1.7 ml of methanol, 0.3 ml of 98% sulfuric acid and 2.0 ml of chloroform for 140 minutes at 100° C. to convert the composition of the P(3HB-co-3HHx) copolymer to the methylester. The reaction solution was then added with 1 ml of water to induce phase separation. Then, the lower layer, which is a chloroform layer, was supplied for gas chromatography. The gas chromatography was carried out using a Shimadzu GC-17A system equipped with a Neutrabond-I capillary column and a flame ionization detector.

Moreover, the molecular weight and polydispersity of the P(3HB-co-3HHx) copolymer accumulated in cells were determined. The molecular weight and polydispersity were determined by gel permeation chromatography (GPC). As a GPC device, a Shimadzu 10A GPC system (manufactured by Shimadzu Corporation) equipped with a Shimadzu RID-10A differential refractometer (manufactured by Shimadzu Corporation) as a detector was used. K-802 (separation range between 150 and 5,000) manufactured by Showa Denko K. K. was connected to Shodex K-806M (separation range between 500 and 20,000,000) in series, and it was used as a separation column. Determination was carried out at a column temperature of 40° C. at a flow rate of 0.8 ml/min., using chloroform as a solvent. A calibration curve used in measurement of the molecular weight was produced, using polystyrenes with low polydispersity that are used in measurement of molecular weight (9 types within the range of Mw=1,320 to 3,150,000). Using this calibration curve, the molecular weights of all samples were calculated in terms of polystyrene.

A sample for measurement was prepared as described below. 20 ml of chloroform was added to 10 mg of dry cells, and the mixture was stirred at room temperature for 48 hours, so as to extract the P(3HB-co-3HHx) copolymer from the cells to the chloroform layer. The chloroform solution containing the P(3HB-co-3HHx) copolymer was passed through a PTFE filter with a pore size of 0.5 μm to eliminate cell components. Thereafter, hexane was added to the filtrate such that the amount of hexane became 2 times greater than that of the filtrate, whereby the P(3HB-co-3HHx) copolymer was deposited and purified. After air-drying, the obtained P(3HB-co-3HHx) copolymer was dissolved in chloroform such that the concentration became 1 mg/ml. The solution was then filtrated through a PTFE filter with a pore size of 0.45 μm to prepare a sample for GPC measurement. The molecular weight of the obtained sample was determined.

The results of the gas chromatography and the measurement of molecular weight are shown in Table 3.

TABLE 3

| Mutant type (amino acid substitution) | PHA content (wt %) | 3HHx fraction (mol %) | Molecular weight Mn(10$^4$) | Mw/Mn |
|---|---|---|---|---|
| Wild type | 2(±1) | 10(±1) | 98.4 | 2.6 |
| E2-13 (Q45L) | 3(±1) | 11(±1) | | |
| T1-34 (D67E) | 2(±1) | 12(±1) | | |
| E1-19 (V148A) | 1(±1) | 9(±1) | | |
| E2-50 (N149S) | 13(±3) | 18(±1) | 48.3 | 4.1 |
| E1-34 (M151T) | 1(±0) | 10(±0) | | |
| T3-27 (K165R) | 2(±0) | 9(±1) | | |
| T3-11 (D171G) | 6(±1) | 16(±0) | 75.0 | 3.5 |
| E1-27 (F203L) | 0.5(±0) | 11(±1) | | |
| T1-44 (T234S) | 2(±0) | 11(±0) | | |
| T3-22 (Y250F) | 2(±0) | 11(±0) | | |
| T3-25 (D295G) | 1(±0) | 11(±1) | | |
| T1-41 (G303S) | 3(±1) | 11(±1) | | |
| T1-12 (R335Q) | 2(±0) | 12(±0) | | |

In Table 3, Mn represents a number-average molecular weight, and Nw represents a weight-average molecular weight. As is clear from Table 3, the wild type *Escherichia* coli LS5218 contained 2% by weight of the P(3HB-co-3HHx) copolymer in terms of the weight of dry cells and had a fraction of 3HHx monomer of 10±1%. On the other hand, E2-50 and T3-11 showed the increase in the content of P(3HB-co-3HHx) copolymer by 6.5 times and 3 times respectively compared to the wild type. In addition, E2-50 and T3-11 had a fraction of 3HHx monomer of 18±1% and 16±0% respectively, which showed the production of copolymers with a higher 3HHx fraction than the wild type.

Moreover, as is clear from Table 3, in the wild type *Escherichia coli* LS5218, the number-average molecular weight of the P(3HB-co-3HHx) copolymer was 98.4 ($\times 10^4$), and the polydispersity was 2.6. In contrast, in the case of E2-50 and T3-11, the number-average moleculars weight of the P(3HB-co-3HHx) copolymers were 48.3 ($\times 10^4$) and 75.0 ($\times 10^4$), respectively. The polydispersities were 4.1 and 3.5, respectively. Thus, it was found that a P(3HB-co-3HHx) copolymer having a molecular weight and polydispersity different from those of the wild type was expressed in the E2-50 and T3-11.

Mutation sites in the mutant type PhaC$_{AC}$ contained in the purified plasmid vector pBSEE32phbAB were identified by carrying out the base sequence determination on the above E2-50 and T3-11. The base sequence determination was carried out by the dideoxy chain termination method using a Prism 310 DNA sequencer or a Prism 377 DNA sequencer, using a BigDye terminator cycle sequencing ready reaction kit (available from Applied Biosystems). The base sequence information obtained by the base sequence determination was analyzed using GENETYX-MAC software (manufactured by Software Development Co., Ltd.) or BLAST (Basic Local Aliginment Search Tool; available from National Center for Biotechnology Information).

As a result, it was found that the mutation for substituting serine for the 149th asparagine was introduced into E2-50. Further, it was found that the mutation for substituting glycine for the 171 st aspartic acid was introduced into T3-11.

All publications, patents and patent applications cited herein are incorporated herein by reference in their entirety.

INDUSTRIAL APPLICABILITY

As described in detail hereinabove, the present invention can provide a method for producing a biodegradable polyester capable of controlling various physical properties of the biodegradable polyester, a method for producing a biodegradable polyester having desired physical properties, a biodegradable polyester obtained by the above described production method and a poly(3-hydroxyalkanoate) biosynthetic mutant enzyme capable of producing the biodegradable polyester having desired physical properties.

The invention claimed is:

1. A mutant poly(3-hydroxyalkanoate) biosynthetic enzyme, comprising the amino acid sequence SEQ ID NO: 1; wherein the asparagine at position 149 is replaced by serine and/or the aspartic acid at position 171 is replaced by glycine.

2. The poly(3-hydroxyalkanoate) biosynthetic mutant enzyme according to claim 1, wherein said 149th amino acid is senne.

3. The poly(3-hydroxyalkanoate) biosynthetic mutant enzyme according to claim 1, wherein said 171st amino acid is glycine.

4. A method for increasing the poly(3-hydroxyalkanoate) content of a biodegradable polyester by at least three-fold, comprising expressing a mutant poly (3-hydroxyalkanoate) biosynthetic enzyme comprising the amino acid sequence of SEQ ID No: 1, wherein the asparagine at position 149 and/or the aspartic acid at position 171 is replaced by other amino acids, in a host to synthesize a biodegradable 3-hydroxy-polyalkanoate polyester copolymer in said host.

5. The method of claim 4, in which the 149$^{th}$ amino acid is serine.

6. The method of claim 4, in which the 171$^{st}$ amino acid is glycine.

7. The method of claim 5, in which the 171$^{st}$ amno acid is glycine.

8. A method for increasing the polydispersity of a biodegradable 3-hydroxypolyalkanoate polyester by at least 30%, comprising expressing a mutant poly(3-hydroxyalkanoate) biosynthetic enzyme comprising the amino acid SEQ ID No: 1, wherein the asparagine at position 149 and/or the aspartic acid at position 171 is replaced by other amino acids, in a host to synthesize a biodegradable 3-hydroxyalkanoate polyester in said host.

9. The method of claim 8, in which the 149$^{th}$ amino acid is serine.

10. The method of claim 8, in which the 171$^{st}$ amino acid is glycine.

11. The method of claim 10, in which the 171$^{st}$ amino acid is glycine.

* * * * *

SEQUENCE LISTING

<160> NUMBER OF SEQ ID NOS: 3

<210> SEQ ID NO 1
<211> LENGTH: 594
<212> TYPE: PRT
<213> ORGANISM: Aeromonas caviae
<220> FEATURE:
<223> OTHER INFORMATION: Inventor: Doi, Yoshiharu; Taguchi, Seiichi; Kichise Tomoyasu

<400> SEQUENCE: 1

```
Met Ser Gln Pro Ser Tyr Gly Pro Leu Phe Glu Ala Leu Ala His Tyr
 1               5                  10                  15

Asn Asp Lys Leu Leu Ala Met Ala Lys Ala Gln Thr Glu Arg Thr Ala
            20                  25                  30

Gln Ala Leu Leu Gln Thr Asn Leu Asp Asp Leu Gly Gln Val Leu Glu
        35                  40                  45

Gln Gly Ser Gln Gln Pro Trp Gln Leu Ile Gln Ala Gln Met Asn Trp
    50                  55                  60

Trp Gln Asp Gln Leu Lys Leu Met Gln His Thr Leu Leu Lys Ser Ala
65                  70                  75                  80

Gly Gln Pro Ser Glu Pro Val Ile Thr Pro Glu Arg Ser Asp Arg Arg
                85                  90                  95

Phe Lys Ala Glu Ala Trp Ser Glu Gln Pro Ile Tyr Asp Tyr Leu Lys
            100                 105                 110

Gln Ser Tyr Leu Leu Thr Ala Arg His Leu Leu Ala Ser Val Asp Ala
        115                 120                 125

Leu Glu Gly Val Pro Gln Lys Ser Arg Glu Arg Leu Arg Phe Phe Thr
    130                 135                 140

Arg Gln Tyr Val Asn Ala Met Ala Pro Ser Asn Phe Leu Ala Thr Asn
145                 150                 155                 160
```

```
Pro Glu Leu Leu Lys Leu Thr Leu Glu Ser Asp Gly Gln Asn Leu Val
                165                 170                 175

Arg Gly Leu Ala Leu Leu Ala Glu Asp Leu Glu Arg Ser Ala Asp Gln
            180                 185                 190

Leu Asn Ile Arg Leu Thr Asp Glu Ser Ala Phe Glu Leu Gly Arg Asp
        195                 200                 205

Leu Ala Leu Thr Pro Gly Arg Val Val Gln Arg Thr Glu Leu Tyr Glu
    210                 215                 220

Leu Ile Gln Tyr Ser Pro Thr Thr Glu Thr Val Gly Lys Thr Pro Val
225                 230                 235                 240

Leu Ile Val Pro Pro Phe Ile Asn Lys Tyr Tyr Ile Met Asp Met Arg
                245                 250                 255

Pro Gln Asn Ser Leu Val Ala Trp Leu Val Ala Gln Gly Gln Thr Val
            260                 265                 270

Phe Met Ile Ser Trp Arg Asn Pro Gly Val Ala Gln Ala Gln Ile Asp
        275                 280                 285

Leu Asp Asp Tyr Val Val Asp Gly Val Ile Ala Ala Leu Asp Gly Val
    290                 295                 300

Glu Ala Ala Thr Gly Glu Arg Glu Val His Gly Ile Gly Tyr Cys Ile
305                 310                 315                 320

Gly Gly Thr Ala Leu Ser Leu Ala Met Gly Trp Leu Ala Ala Arg Arg
                325                 330                 335

Gln Lys Gln Arg Val Arg Thr Ala Thr Leu Phe Thr Thr Leu Leu Asp
            340                 345                 350

Phe Ser Gln Pro Gly Glu Leu Gly Ile Phe Ile His Glu Pro Ile Ile
        355                 360                 365

Ala Ala Leu Glu Ala Gln Asn Glu Ala Lys Gly Ile Met Asp Gly Arg
    370                 375                 380

Gln Leu Ala Val Ser Phe Ser Leu Leu Arg Glu Asn Ser Leu Tyr Trp
385                 390                 395                 400

Asn Tyr Tyr Ile Asp Ser Tyr Leu Lys Gly Gln Ser Pro Val Ala Phe
                405                 410                 415

Asp Leu Leu His Trp Asn Ser Asp Ser Thr Asn Val Ala Gly Lys Thr
            420                 425                 430

His Asn Ser Leu Leu Arg Arg Leu Tyr Leu Glu Asn Gln Leu Val Lys
        435                 440                 445

Gly Glu Leu Lys Ile Arg Asn Thr Arg Ile Asp Leu Gly Lys Val Lys
    450                 455                 460

Thr Pro Val Leu Leu Val Ser Ala Val Asp Asp His Ile Ala Leu Trp
465                 470                 475                 480

Gln Gly Thr Trp Gln Gly Met Lys Leu Phe Gly Gly Glu Gln Arg Phe
                485                 490                 495

Leu Leu Ala Glu Ser Gly His Ile Ala Gly Ile Ile Asn Pro Pro Ala
            500                 505                 510

Ala Asn Lys Tyr Gly Phe Trp His Asn Gly Ala Glu Ala Glu Ser Pro
        515                 520                 525

Glu Ser Trp Leu Ala Gly Ala Thr His Gln Gly Gly Ser Trp Trp Pro
    530                 535                 540

Glu Met Met Gly Phe Ile Gln Asn Arg Asp Glu Gly Ser Glu Pro Val
545                 550                 555                 560

Pro Ala Arg Val Pro Glu Glu Gly Leu Ala Pro Ala Pro Gly His Tyr
                565                 570                 575
```

```
Val Lys Val Arg Leu Asn Pro Val Phe Ala Cys Pro Thr Glu Glu Asp
            580                 585                 590
Ala Ala

<210> SEQ ID NO 2
<211> LENGTH: 17
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 2
gctgctgcag accaatc                                                    17

<210> SEQ ID NO 3
<211> LENGTH: 18
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 3
gcctcatttt gcgcctcg                                                   18
```